United States Patent
Baba et al.

(10) Patent No.: US 12,188,944 B2
(45) Date of Patent: Jan. 7, 2025

(54) BACKGROUND REDUCTION IN TOP-DOWN ANTIBODY ANALYSIS

(71) Applicant: DH Technologies Development PTE. LTD., Singapore (SG)

(72) Inventors: Takashi Baba, Richmond Hill (CA); Pavel Ryumin, Toronto (CA)

(73) Assignee: DH TECHNOLOGIES DEVELOPMENT PTE. LTD., Singapore (SG)

( * ) Notice: Subject to any disclaimer, the term of this patent is extended or adjusted under 35 U.S.C. 154(b) by 673 days.

(21) Appl. No.: 17/440,130

(22) PCT Filed: May 13, 2020

(86) PCT No.: PCT/IB2020/054543
§ 371 (c)(1),
(2) Date: Sep. 16, 2021

(87) PCT Pub. No.: WO2020/230063
PCT Pub. Date: Nov. 19, 2020

(65) Prior Publication Data
US 2022/0155318 A1 May 19, 2022

Related U.S. Application Data

(60) Provisional application No. 62/847,130, filed on May 13, 2019.

(51) Int. Cl.
*G01N 33/68* (2006.01)
*H01J 49/42* (2006.01)

(52) U.S. Cl.
CPC ...... *G01N 33/6854* (2013.01); *H01J 49/4215* (2013.01); *H01J 49/426* (2013.01)

(58) Field of Classification Search
CPC . G01N 33/6854; H01J 49/4215; H01J 49/426
See application file for complete search history.

(56) References Cited

U.S. PATENT DOCUMENTS 4,090,075 A 5/1978 Brinkmann
6,194,717 B1 2/2001 Hager
(Continued)

OTHER PUBLICATIONS

Supplementary European Search Report for European Application No. 20805987 dated Dec. 19, 2022.
(Continued)

*Primary Examiner* — Nicole M Ippolito
(74) *Attorney, Agent, or Firm* — Reza Mollaaghababa; Brian Hairston; Potomac Law Group, PLLC

(57) ABSTRACT

Method and devices for performing top down analysis of an antibody are described which involve utilizing an ion source to generate a plurality of ions from a sample containing at least one intact antibody. Further, transmitting said plurality of ions through a quadrupole rod set while applying an RF signal thereto and in the absence of a resolving DC voltage so as to preferentially transmit precursor ions having an m/z value greater than a low mass cutoff of about 1500 m/z from the quadrupole rod set to an ECD cell. The method and device can also performing an ECD reaction in the ECD cell on said precursor ions and also detect reaction products from the ECD reaction.

20 Claims, 5 Drawing Sheets

(56) References Cited

U.S. PATENT DOCUMENTS

| | | |
|---|---|---|
| 2017/0125225 A1 | 5/2017 | Brown et al. |
| 2017/0263431 A1 | 9/2017 | Baba |
| 2018/0095092 A1 | 4/2018 | Baba |
| 2021/0239707 A1* | 8/2021 | Loboda .............. G01N 33/6848 |
| 2021/0285956 A1* | 9/2021 | Bajic ................. G01N 33/6857 |

OTHER PUBLICATIONS

Yuan Mao et al., "Top-Down Structural Analysis of an Intact Monoclonal Antibody by Electron Capture Dissociation-Fourier Transform Ion Cyclotron Resonance Mass-Spectrometry", Analytical Chemistry, vol. 85, No. 9, p. 4239-4246, Apr. 3, 2013 (Abstract).
International Search Report mailed Aug. 31, 2020 in corresponding PCT App. No. PCT/IB2020/054543 (5 pages).
Written Opinion of the International Searching Authority mailed Aug. 31, 2020 in corresponding PCT App. No. PCT/IB2020/054543 (6 pages).
Bateman, R.H. et al., "A novel precursor ion discovery method on a hybrid quadrupole orthogonal acceleration time-of-flight (Q-TOF) mass spectrometer for studying protein phosphorylation," American Society for Mass Spectrometry, Jun. 11, 2002, vol. 13, pp. 792-803.
Huang, Teng-Yi et al., "Top-down protein characterization facilitated by ion/ion reactions on a quadrupole/time of flight platform," Proteomics, 2010, vol. 10, pp. 3577-3588.
Mao, Yuan et al., "Top-down structural analysis of an intact monoclonal antibody by electron capture dissociation- fourier transform ion cyclotron resonance-mass spectrometry," Analytical Chemistry, Apr. 3, 2013, vol. 85, pp. 4239-4246.

* cited by examiner

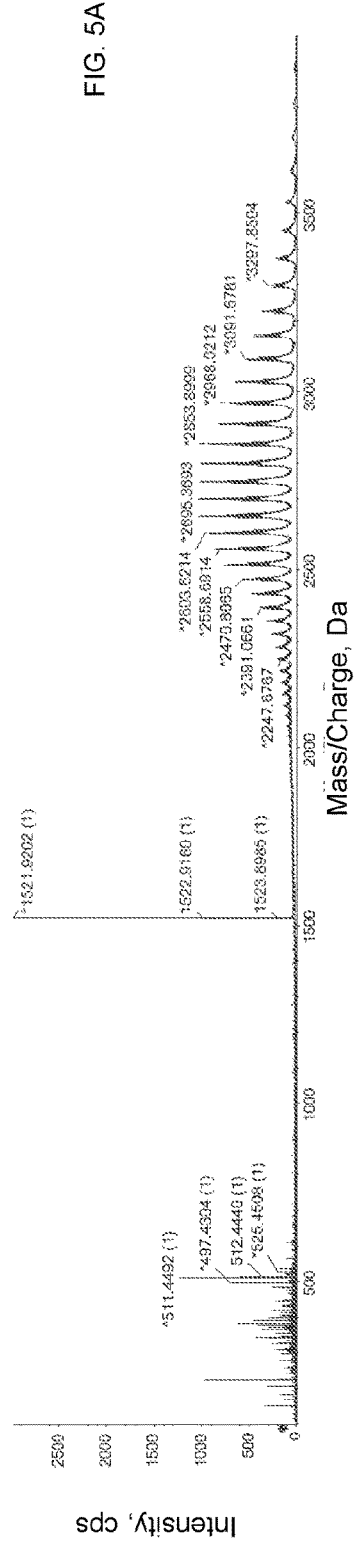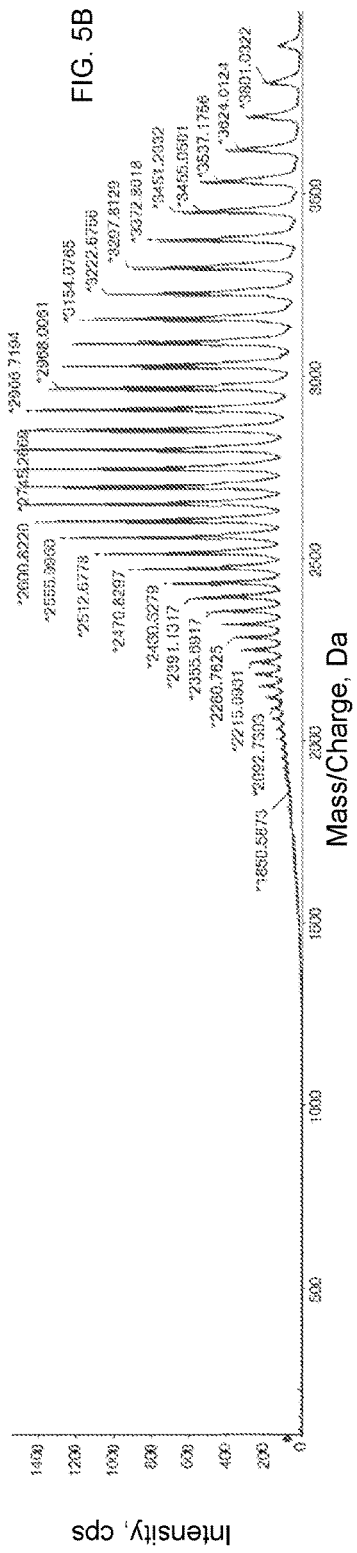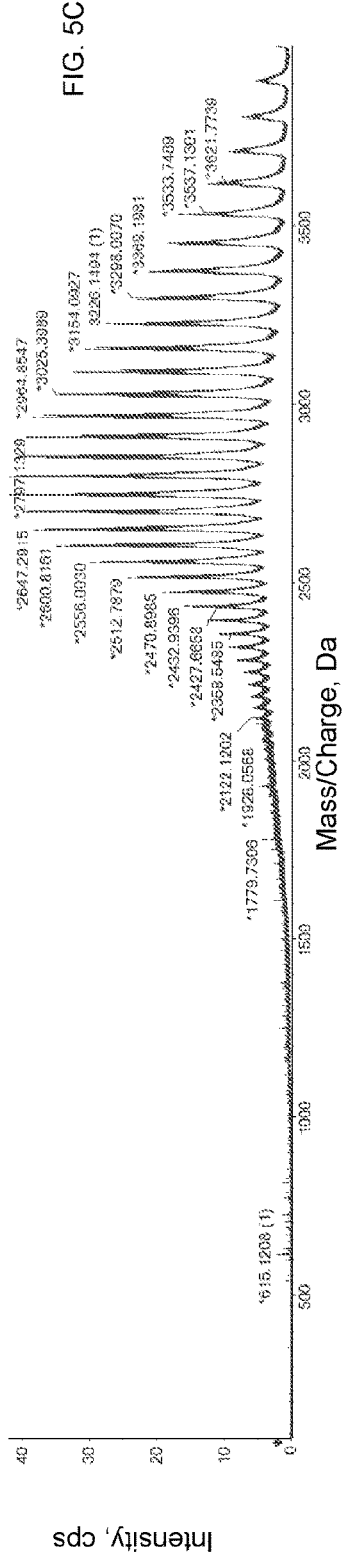

BACKGROUND REDUCTION IN TOP-DOWN ANTIBODY ANALYSIS

RELATED APPLICATIONS

This application is the national stage of International Application No. PCT/IB2020/054543 filed on May 13, 2020, which claims the benefit of priority from U.S. Provisional Application No. 62/847,130, filed on May 13, 2019, the entire contents of which are incorporated by reference herein in their entireties.

FIELD

The invention relates to methods and apparatus utilizing electron capture dissociation (ECD) in the mass spectrometric analysis of intact antibodies.

INTRODUCTION

Mass spectrometry (MS) is an analytical technique for determining the elemental composition of test substances that has both quantitative and qualitative applications. For example, MS can be used to identify unknown compounds and/or determine the structure of a particular compound by observing its fragmentation. Recently, MS has played an increasingly important role in proteomics due to the speed, specificity, and sensitivity of MS strategies in characterizing and identifying peptides and proteins.

One strategy in characterizing proteins in MS-based proteomics is a "bottom-up" approach in which protein(s) of interest are subject to enzymatic digestion (e.g., via trypsin, LysC, etc.) and one or more separations (e.g., multi-dimensional LC) prior to subjecting the peptide fragments to MS analysis ($MS^1$) or tandem MS/MS analysis ($MS^2$). In a "bottom up" $MS^2$ workflow, collision induced dissociation (CID) has been conventionally utilized to further dissociate the precursor peptide fragments selected in the first MS stage into product ion fragments. The amino acid sequence of the precursor peptide ion can then be deduced from the masses of the product ion fragments. In CID, energetic collisions between the ionized precursors ions and inert neutral gas and/or nitrogen molecules vibrate and eventually dissociate (cleave) backbone amide bonds, thereby yielding b-type (N-terminal) and y-type (C-terminal) product ions. By identifying several of the product ion peptides, the original proteins can be determined (e.g., by referencing known sequences in a protein or genome database). However, because CID reactions generally occur only at the weakest peptide amide bonds, incomplete fragmentation along the peptide backbone can make complete reconstruction of the peptide sequence difficult. Another key limitation to the use of CID in proteomics is the loss of post-translational modifications (PTMs) during the dissociation. PTMs (e.g., phosphorylated or sulfated functional groups), which are often only weakly bound to the peptide backbone, can be stripped from the peptide during fragmentation, thereby preventing the detection and characterization of PTMs in the $MS^2$ spectra.

As opposed to the above-described "bottom up" approach, an alternative MS-based proteomics strategy utilizes a "top down" analysis in which intact proteins are instead subjected to dissociation in a mass spectrometer utilizing ion-ion interactions, for example. While conventional CID generally dissociates too few sites to provide complete information to characterize the intact proteins' entire amino acid sequence, ion-ion interactions may be more effective for "top-down" sequencing of intact proteins due to a more complete fragmentation of the peptide backbone. One possible obstacle to "top down" approaches, however, is the wide distribution of the masses of the various multiply-charged precursors following ionization and the complexity of the $MS^2$ spectra. Moreover, real-world applications involve complex, unknown samples, which can add further ambiguity in the analysis of the $MS^2$ spectra.

Accordingly, there remains a need for improved methods and apparatus for mass spectrometric analysis of antibodies utilizing a top-down approach.

SUMMARY

In accordance with various aspects of the present teachings, methods and systems for performing top down MS-based analysis of antibodies are provided herein. In certain aspects, the method comprises utilizing an ion source to generate a plurality of ions from a sample containing at least one intact antibody and transmitting said plurality of ions through a quadrupole rod set while applying an RF signal thereto and in the absence of a resolving DC voltage so as to preferentially transmit precursor ions having an m/z value greater than a low mass cutoff of about 1500 m/z from the quadrupole rod set to an ECD cell. An ECD reaction is then performed in the ECD cell on the precursor ions and the reaction products from the ECD reaction are detected. In various implementations, the quadrupole rod set comprises Q1 in a triple quadrupole. In certain aspects, the amplitude and/or the frequency of the RF signal is adjusted such that the low mass cutoff is about 1700 m/z. Alternatively, the amplitude and/or the frequency of the RF signal is adjusted such that the low mass cutoff is about 2000 m/z. In some aspects, at least a portion of the reaction products have an m/z below the low mass cutoff.

In some implementations, performing an ECD reaction comprises introducing electrons into the ECD cell while transmitting said precursor ions therethrough.

In certain aspects, the plurality of precursor antibody ions comprise a plurality of charge states. For example, in certain aspects, the plurality of precursor antibody ions can comprise antibodies of the same species of antibody but exhibiting at least two different m/z in a range from about 2000 to about 4000.

In various aspects of the present teachings a mass spectrometer system is provided comprising an ion source for generating a plurality of ions from a sample containing intact antibodies; a quadrupole rod set extending along a central longitudinal axis and configured to receive said plurality of ions from said ion source through an inlet end and to transmit at least a portion of said ions through an outlet end, the quadrupole rod set comprising a first pair of elongate rods and a second pair of elongate rods disposed around and parallel to the central longitudinal axis; an ECD cell for receiving ions transmitted from the quadrupole rod set and within which said ions received from the quadrupole rod set are reacted with electrons to generate product ions therefrom; and a detector for detecting said product ions. A power system electrically coupled to the quadrupole rod set is configured to provide an RF signal to the quadrupole rod set in the absence of a resolving DC voltage so as to substantially prevent ions having a m/z value less than a low mass cutoff of about 1500 m/z from being transmitted from the quadrupole rod set to the ECD cell. In some implementations, the low mass cutoff can be higher than 1500 m/z. For example, in some implementations, the power system is configured to provide an RF signal to the quadrupole rod set in the absence of a resolving DC voltage to substantially prevent ions having a m/z value less than a low mass cutoff of about 1700 m/z from being transmitted from the quadrupole rod set to the ECD cell. In other implementations, the power system is configured to provide an RF signal to the quadrupole rod set in the absence of a resolving DC voltage to substantially prevent ions having a m/z value less than a low mass cutoff of about 2000 m/z from being transmitted from the quadrupole rod set to the ECD cell. Additionally, the system can comprise a controller to adjust the low mass cutoff. For example, the controller is configured to increase the amplitude of the RF signal to increase the low mass cutoff in some embodiments. In various implementations, the amplitude of the RF signal is in a range from about 0.1 $kV_{p-p}$ to about 10 $kV_{p-p}$.

In some implementations, the quadrupole rod set comprises Q1. Additionally, in some aspects, the quadrupole rod set is housed within a chamber maintained at a pressure less than about $1 \times 10^{-4}$ Torr. An electron source is included in the system for introducing electrons into the ECD cell.

In various aspects, the intact antibodies may have an m/z in a range from about 2000 to about 4000. Additionally, at least a portion of said product ions have an m/z below said low mass cutoff in some implementations.

Each of the features described above may be paired and/or combined and/or removed in various ways to the specific embodiments described to arrive at alternative embodiments that should be considered to be within the scope of the present teachings.

These and other features of the applicant's teaching are set forth herein.

BRIEF DESCRIPTION OF THE DRAWINGS

The foregoing and other objects and advantages of the invention will be appreciated more fully from the following further description, with reference to the accompanying drawings. The skilled person in the art will understand that the drawings, described below, are for illustration purposes only. The drawings are not intended to limit the scope of the applicant's teachings in any way.

FIGS. 5A-C depicts exemplary mass spectra of a sample containing an antibody to be analyzed in accordance with the present teachings.

DETAILED DESCRIPTION

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicant's teachings in any manner. As used herein, the terms "about" and "substantially equal" refer to variations in a numerical quantity that can occur, for example, through measuring or handling procedures in the real world; through inadvertent error in these procedures; through differences in the manufacture, source, or purity of compositions or reagents; and the like. Typically, the terms "about" and "substantially" as used herein means greater or lesser than the value or range of values stated by ⅒ of the stated values, e.g., ±10%. For instance, a concentration value of about 30% or substantially equal to 30% can mean a concentration between 27% and 33%. The terms also refer to variations that would be recognized by one skilled in the art as being equivalent so long as such variations do not encompass known values practiced by the prior art.

In various aspects, methods and systems are provided herein for analyzing ions so as to enable ECD-based top-down analysis of intact antibodies. Whereas conventional methods of MS-based proteomics can result in convoluted and/or inaccurate data due to the presence of interfering species as well as multiply-charged precursor ions of different charge states, the present teachings can result in a less-convoluted mass spectrum while generating a complete sequence for antibody ions utilizing the high dissociation efficiency of ECD. As discussed in detail below, various aspects of the methods and systems disclosed herein selectively prevent ions exhibiting a m/z below a low mass cutoff (LMCO) from entering the ECD cell, and allowing transmission of ions formed from the intact antibodies regardless of their charge states.

Figure 1:
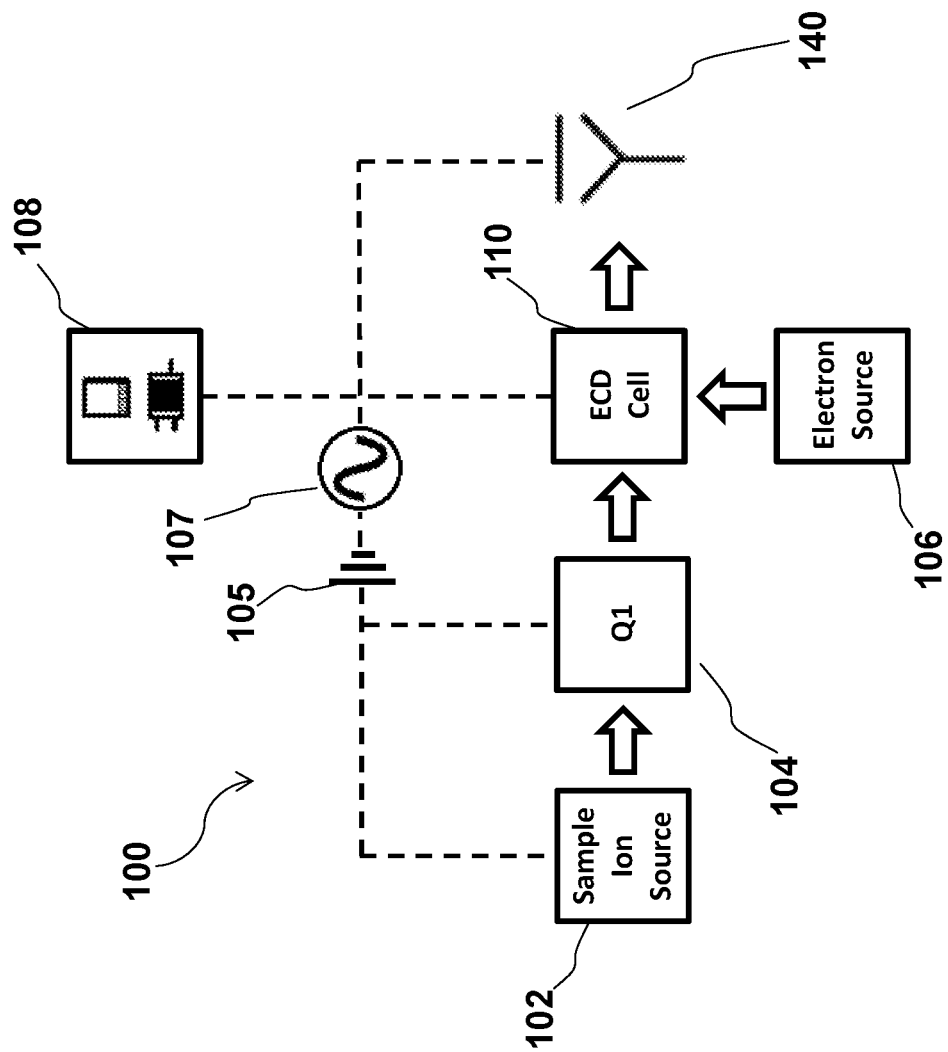
FIG. 1 schematically depicts an exemplary ECD-mass spectrometer system in accordance with various aspects of the applicant's teachings.

While the systems, devices, and methods described herein may be used in conjunction with many different mass spectrometer systems with fewer, more, or different components than those depicted, an exemplary mass spectrometer system 100 for use in accordance with the present teachings is illustrated schematically in FIG. 1. As shown in the exemplary embodiment depicted in FIG. 1, the mass spectrometer system 100 generally comprises a sample ion source 102 for ionizing a sample containing or suspected of containing one or more antibodies of interest so as to generate a plurality of precursor ions therefrom and a quadrupole rod set 104 for receiving the generated ions from the ion source 102, which then transmits a portion of the generated ions to an ECD reaction cell 110. The ECD cell 110 includes an interaction region within which the precursor cations interact with electrons generated by electron source 106 so as to dissociate the precursor ions into a plurality of product ions detected by the detector 140. As shown in FIG. 1, the exemplary mass spectrometer system 100 additionally includes one or more power supplies (e.g., DC power supply 105 and RF power supply 107) that are controlled by the controller 108 so as to apply electric potentials with RF, AC, and/or DC components to electrodes of the various components to configure the elements of the mass spectrometer system 100 in a coordinated fashion and/or for various different modes of operation. As discussed in detail below, in exemplary implementations of the present teachings, the electrical signals applied to the quadrupole rod set 104 are set and/or adjusted so as to preferentially transmit to the ECD cell 110 those precursor ions having a m/z value greater than a LMCO (e.g., about 1500 m/z). In particular implementations, an RF signal exhibiting an amplitude and frequency is applied to the various rods of the quadrupole rod set and in the absence of a DC resolving voltage to these rods, with the amplitude and frequency being selected so as to substantially prevent ions having a m/z value below the LMCO from being transmitted into downstream elements, thereby eliminating these low m/z ions from interfering with subsequent analysis and/or interpretation of the $MS^2$ spectra generated by the detection of product ions following reaction of the antibody precursor ions in the ECD cell 110.

The ion source 102 may have a variety of configurations but is generally configured to generate ions (e.g., cations) from antibodies contained within a sample. In certain implementations, suitable sample sources for use in accordance with the present teachings are configured to contain and/or introduce a sample (e.g., a solution containing or suspected of containing an antibody of interest) to the ion source 102, for example, via fluid coupling so as to transmit a liquid sample to the ion source 102 through one or more conduits, channels, tubing, pipes, capillary tubes, etc. By way of non-limiting examples, the sample source comprises a reservoir of the sample to be analyzed or an input port through which the sample is injected. In some aspects, for example, the sample source comprises an infusion pump (e.g., a syringe pump) for continuously flowing the sample into the ion source 102. Alternatively, also by way of non-limiting example, the liquid sample to be analyzed is in the form of an eluent from an on-line liquid chromatography column, though in some aspects, one or more sample preparation steps (e.g., multi-dimensional LC separations, electrophoresis, di-sulfide bond reduction, etc.) may be performed off-line.

In some exemplary aspects of the present teachings, the ion source 102 includes a conduit in direct or indirect fluid communication with the sample source that terminates in an outlet end that at least partially extends into an ionization chamber. As the liquid sample is discharged from the outlet end into the ionization chamber (e.g., as a plurality of micro-droplets), antibodies (and other interfering analytes) contained within the micro-droplets are ionized (i.e., charged) by the ion source 102. As the liquid (e.g., a solvent) within the droplets evaporates, the ions are released and drawn toward and through an aperture for transmission to the quadrupole rod set 104 and ECD cell 110. It will be appreciated that a number of different devices known in the art and modified in accordance with the teachings herein may be utilized as the ion source 102. By way of non-limiting example, the ion source 102 may be a electrospray ionization device, a nebulizer assisted electrospray device, a chemical ionization device, a nebulizer assisted atomization device, a photoionization device, a laser ionization device, a thermospray ionization device, and a sonic spray ionization device.

As shown in the implementation of FIG. 1, the system 100 includes an ECD cell 110 within which precursor ions transmitted by the quadrupole rod set 104 can be subject to an ECD reaction. An ECD reaction normally involves a multiply protonated molecule M interacting with a free electron to form radical species with odd number of electrons:

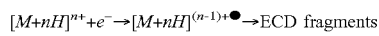

Adding an electron to an incomplete molecular orbital of the precursor antibody cation releases binding energy which, if sufficient to exceed a dissociation threshold, causes the fragmentation of the electron acceptor ion as is known in the art. Once precursor ions are reacted within the ECD cell 110, the fragment or product ions can be transferred to one or more mass analyzers for further analysis prior to detection of the ECD product ions by the detector 110. By way of example, a mass analyzer disposed between the ECD cell 110 and the detector 140 can comprise any suitable mass spectrometer module including, but not limited to, a time of flight (TOF) mass spectrometry module, a quadrupole mass spectrometry module, a linear ion trap (LIT) module and the like, for example, for scanning the product ions therefrom. By way of non-limiting example, ECD reactions can be performed in the ECD devices described in PCT Pub. No. WO2014191821 entitled "Inline Ion Reaction Device Cell and Method of Operation," the teachings of which is incorporated by reference in their entireties. Consistent with the need to provide electrons to the ECD cell 110 for the ECD reaction, the system 100 additionally includes an electron source 106. Those skilled in the art will appreciate that any electron source suitable for use in a mass spectrometer system for providing electrons for ion-ion reactions and modified in accordance with the present teachings may be utilized in system 100. By way of non-limiting example, electrons may be generated by a filament (e.g., tungsten, thoriated tungsten, and others) or another electron emitter, such as $Y_2O_3$ cathode. In an exemplary operation, an electric current of 1 to 3 A can be applied to heat the electron source, which produces 1 to 10 W heat power so as to generate electrons. It will be appreciated that the electron source 106 may, in some aspects, additionally be associated with a magnetic field generator (e.g., a permanent neodymium magnet or an electromagnet, not shown) to control the path of the electrons within the ECD cell 110 and a cooling mechanism (e.g., heat sink, active cooling) to maintain the temperature of a magnet, if present, lower than its Curie temperature at which the magnetization of permanent magnet is lost. Other known methods of cooling the magnet may also be utilized.

As shown, the system 100 includes a detector 140 (e.g., a time-of-flight mass analyzer, an ion trap mass analyzer, a Faraday cup or other ion current measuring device) effective to detect the precursor and/or product ions transmitted from the ECD cell 110. The detected ion data may be stored in memory and analyzed by a computer or computer software.

As will be appreciated by a person skilled in the art, the system 100 may additionally include any number of additional mass analyzer elements or ion optical elements disposed upstream or downstream of the quadrupole rod set 104 and ECD cell 110 for further ion processing, manipulation, and/or mass analysis. By way of example, ions may be transported through one or more additional differentially pumped vacuum stages (e.g., a first stage maintained at a pressure of approximately 2.3 Torr, a second stage maintained at a pressure of approximately 6 mTorr, and a third stage maintained at a pressure of approximately $10^{-5}$ Torr, with the third cell containing the detector 140 and two or more quadrupole mass analyzers having the ECD cell 110 located therebetween). For instance, in one embodiment, the quadrupole rod set 104 represents Q1 (maintained at a pressure less than about $1 \times 10^{-4}$ Torr) and the ECD cell 110 represents or replaces Q2 within a Q-q-Q triple quadrupole mass spectrometer (see e.g., Baba et al., "Electron Capture Dissociation in a Radio Frequency Ion Trap," Anal. Chem. 2004 Aug. 1; 76(15): 4263-6 and PCT Pub. No.

WO2014191821 entitled "Inline Ion Reaction Device Cell and Method of Operation," the teachings of each of these exemplary references describing ECD devices incorporated by reference in their entireties).

As shown, the depicted system 100 additionally includes a controller 108 operatively coupled to one or more of the elements of the system 100 so as to control the operation thereof. By way of example, the controller 108 may include a processor for processing information, data storage for storing mass spectra data, and instructions to be executed. As discussed in detail below and as generally known in the art and modified in accordance with the present teachings, the controller 108 may control the generation of ions by the sample ion source 102 and of electrons by the electron source 106 and/or to control the movement of ions into and through the quadrupole rod set 104 and ECD cell 110 via the application of one or more RF/DC voltages to electrodes thereof, by way of example. It will be appreciated that though controller 108 is depicted as a single component, one or more controllers (whether local or remote) may be configured to cause the mass spectrometer system 100 to operate in accordance with any of the methods described herein. Additionally, in some implementations, the controller 108 may be operatively associated with an output device such as a display (e.g., a cathode ray tube (CRT) or liquid crystal display (LCD) for displaying information to a computer user) and/or an input device including alphanumeric and other keys and/or cursor control for communicating information and command selections to the processor. Consistent with certain implementations of the present teachings, the controller 108 executes one or more sequences of one or more instructions contained in data storage, for example, or read into memory from another computer-readable medium, such as a storage device (e.g., a disk). The one or more controller(s) may take a hardware or software form, for example, the controller 108 may take the form of a suitably programmed computer, having a computer program stored therein that is executed to cause the mass spectrometer system 100 to operate as otherwise described herein, though implementations of the present teachings are not limited to any specific combination of hardware circuitry and software. Various software modules associated with the controller 108, for example, may execute programmable instructions to perform the exemplary methods described below with reference to FIG. 4.

Figure 2:
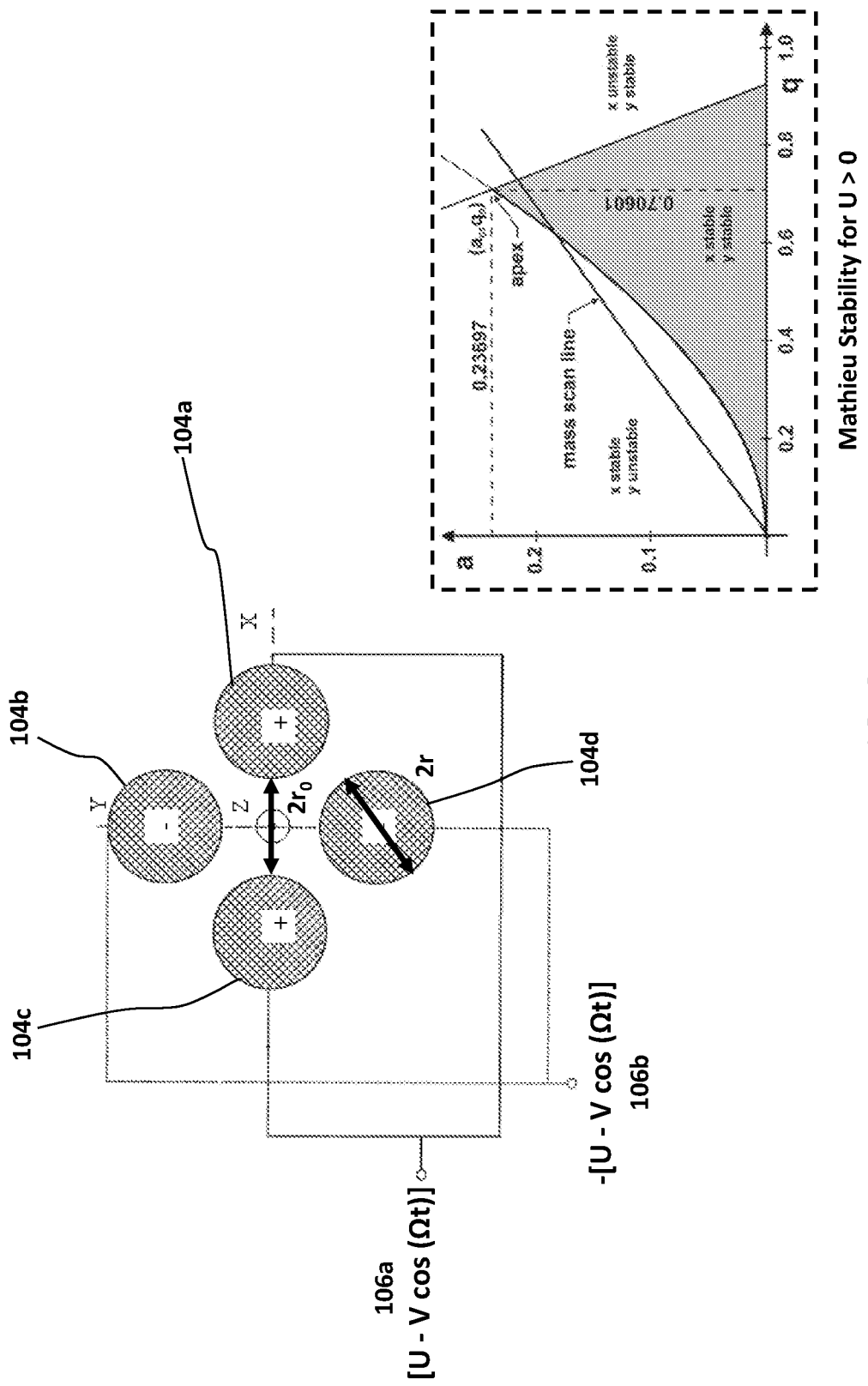
FIG. 2 schematically depicts an exemplary quadrupole suitable for use in the system of FIG. 1 according to various aspects of the present teachings.

As noted above, the exemplary mass spectrometer system 100 includes one or more power supplies that are controlled by the controller 108 so as to apply electric potentials with RF, AC, and/or DC components to electrodes of the various components to configure the elements of the mass spectrometer system 100 in a coordinated fashion and/or for various different modes of operation, as discussed otherwise herein. With reference now to FIG. 2, the exemplary quadrupole rod set 104 includes four rods 104a-d that are disposed around and parallel to a central longitudinal axis (Z) extending from an inlet end (e.g., toward the ion source) to an outlet end (e.g., toward the ECD cell). The rods 104a-d comprise rods having a cylindrical shape (i.e., a circular cross-section of radius r as shown in FIG. 2) disposed equidistant from the central axis (Z), with each of the rods 104a-d being equivalent in size and shape to one another. The minimum distance between each of the rods 104a-d and the central axis (Z) is defined by the distance $r_0$ such that the innermost surface of each primary rod 104a-d is separated from the innermost surface of the other rod in its rod pair across the central longitudinal axis (Z) by a minimum distance of $2r_0$. In some exemplary implementations, the $r_0$ of a the rod set 104 is in a range from about 3 mm to about 10 mm. It will be appreciated that though the rods 104a-d are depicted as cylindrical, the cross-sectional shape, size, and/or relative spacing of the rods 104a-d may be varied as is known in the art. For example, in some aspects, the rods 104a-d can exhibit a radially internal hyperbolic surface according to the equation $x^2-y^2=r_0^2$, where $r_0$ (the field radius) is the radius of an inscribed circle between the electrodes in order to generate quadrupole fields.

The rods 104a-d are electrically conductive (i.e., they can be made of any conductive material such as a metal or alloy) and can be coupled to a power system (comprising one or more power supplies 105, 107 of FIG. 1) such that one or more electrical signals can be applied to each rod 104a-d alone or in combination. In particular, the rods 104a-d generally comprise two pairs of rods (e.g., a first pair comprising rods 104a and 104c and a second pair comprising rods 104b and 104d), with rods of each pair being disposed on opposed sides of the central axis (Z) and to which identical electrical signals can be applied. For example, in some aspects as illustrated in FIG. 2, the power system can comprise a power supply 106a electrically coupled to the first pair of rods 104a,c so as to apply identical electric potentials thereto and a power supply 106b electrically coupled to the second pair of rods 104b,d for applying a different electrical signal thereto. As shown in FIG. 2, in some implementations the exemplary power system can apply an electric potential to the first pair of rods 104a,c of [U−V cos Ωt], where U is the magnitude of the DC electrical signal, V is the zero-to-peak amplitude of the AC or RF signal, Ω is the frequency of the AC or RF signal, and t is time. Similarly, the exemplary power system can apply an electric potential to the second pair of rods 104b,d of −[U−V cos Ωt]. In this exemplary configuration, the electrical signals applied to the first pair of rods 104a,c and the second pair of rods 104b,d differ in the polarity of the DC signal (i.e., the sign of U), while the RF portions of the electrical signals would be 180° out of phase with one another. It will thus be appreciated by a person skilled in the art that the quadrupole rod set 104 may in some aspects be thought of a quadrupole mass filter that can selectively transmit ions of a selected m/z range by a suitable choice of the DC/RF ratio. For example, considering the DC electrical signals applied to the four primary rods 104a-d alone (i.e., ±U), a cation injected into the quadrupole rod set 104 as shown in FIG. 2 would experience a stabilizing force (toward the central axis Z) in the X-Z plane based on the application of a positive DC voltage to the first pair of electrodes 104a,c, while the cation would experience a destabilizing force in the Y-Z plane based on the application of a negative DC voltage to the second pair of electrodes 104b,d. Considering the effect of the RF signal alone, a cation would be sequentially attracted and repelled by the various rod pairs 104a,c and 104b,d as the RF signals applied to the rod pairs change over time. Because cations of low m/z are more easily able to follow the alternating component of the field, low m/z cations would tend to stay more in phase with the RF signal, gain energy from the field, and oscillate with increasingly large amplitude until they encounter one of the rods 104a-d and are discharged. Now, considering the effect of the combined DC and RF signals, it will be appreciated that the field in the X-Z plane would function as a high-pass mass filter in that only ions of high m/z will be transmitted to the other end of the quadrupole without striking the first pair of electrodes 104a,c. On the other hand, in the Y-Z plane, cations of high m/z will be unstable because of the defocusing/attractive effect of the negative DC voltage, though some ions of lower m/z may be stabilized by the RF component if its amplitude is set so as to correct the trajectory whenever the cation's deviation increases. Thus, the field in the Y-Z plane can be said to function as a low-pass mass filter in that only ions of lower m/z will be transmitted to the other end of the quadrupole rod set 104 without striking the second pair of rods 104b,d.

By a suitable choice of the RF/DC ratio of the electrical signals applied to the quadrupole rod set 104, the two effects described above in the X-Z plane and Y-Z plane together provide a mass filter capable of resolving individual atomic masses, as depicted in the exemplary inset Mathieu stability diagram of the following parameters:

$$a = a_x = -a_y = \frac{4eU}{mr_0^2 \Omega^2} \quad (1)$$

$$q = q_x = q_y = \frac{2eV}{mr_0^2 \Omega^2} \quad (2)$$

where e is the charge on an electron, U is the amplitude of the DC voltage, V is the applied zero-to-peak RF voltage, m is the mass of the ion, $r_0$ is the effective radius between rods 104a-d, and $\Omega$ is the applied RF frequency. It should be noted that the parameters a and q are proportional to the DC voltage U and the RF voltage V, respectively, and that q=0.908 at the stability boundary in the Mathieu stability diagram.

Figure 3:
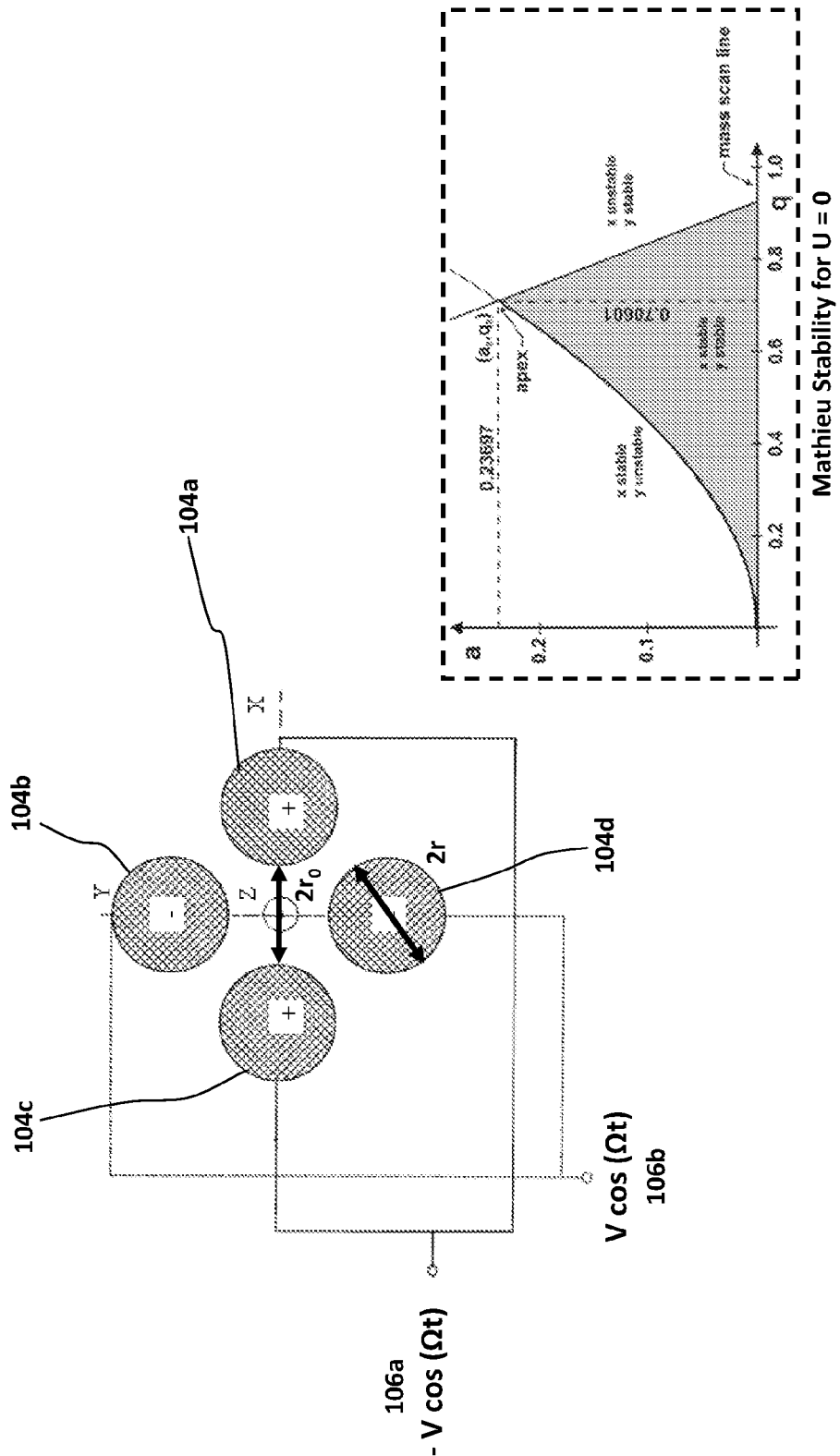
FIG. 3 schematically depicts the exemplary quadrupole of FIG. 2 operating in RF-only mode according to various aspects of the present teachings.

As noted above, the exemplary mass spectrometer system 100 includes one or more power supplies that is controlled by the controller 108 so as to apply electric potentials with RF, AC, and/or DC components to electrodes of the various components to configure the elements of the mass spectrometer system 100 in a coordinated fashion and/or for various different modes of operation, as discussed otherwise herein. Though FIG. 2 depicts both a DC signal (i.e., ±U) and an RF signal (i.e., ±[U−V cos Ωt]) being applied to the rods 104a-d of the quadrupole rod set 104 during a mass filter implementation (e.g., by ramping U and V), the present teachings provide systems and methods in which the electrical signals are applied to the various rods of the quadrupole rod set 104 without a DC resolving voltage during periods of establishing a LMCO and the preferential transmission of ions above the LMCO m/z. With reference now to FIG. 3, the quadrupole rod set 104 is shown in such an RF-only configuration in which those ions having a m/z greater than the LMCO are preferentially transmitted to the ECD cell 110 for further processing as discussed otherwise herein. That is, as depicted in FIG. 3, the DC signal (U) is set to 0 V, such that the parameter a from Eq. (1) becomes zero. Under these conditions in which a RF-only signal exhibiting a peak-to-peak amplitude (V) and frequency (Ω) is applied to the various rods 104a-d, the mass scan line becomes horizontal as shown in the inset Mathieu stability diagram of FIG. 3 such that ions entering the quadrupole rod set 104 that are stable at and below $q_{max}$=0.908 are selectively transmitted to the ECD 110. In other words, by rearranging Eq. (2) above and substituting 0.908 for q, the $m/e_{LMCO}$ according to the following formula represents the ions of lowest mass/charge ratio that are transmitted by quadrupole rod set 104:

$$m/e_{LMCO} = \frac{2V}{(0.908)r_0^2 \Omega^2} \quad (3)$$

By a suitable choice of the RF amplitude (V) and frequency (Ω) applied to the quadrupole rod set 104 in accordance with various aspects of the present teachings, the LMCO can be set and/or adjusted to substantially prevent low m/z ions from being transmitted into downstream elements, thereby eliminating interference with subsequent analysis and/or interpretation of the spectra generated by the detection of product ions following reaction of the higher m/z antibody precursor ions in the ECD cell 110. In some aspects, for example, the amplitude and frequency of the RF signal may be set such that ions exhibiting m/z greater than 1500, greater than 1700, or greater than 2000 may be selectively transmitted by the quadrupole rod set 104. Exemplary combinations of V and Ω include an RF amplitude in a range from about 0.1 $kV_{p-p}$ to about 10 $kV_{p-p}$ and/or an RF frequency in a range from about 0.8 MHz to about 3 MHz, with the values being selected for example based on the quadrupole's effective field radius and desired LMCO, by way of example, according to Eq. (3) above. In one exemplary implementation to obtain an LMCO equal to about 1500 m/z, the field radius ($r_0$) can be 0.4 mm, the RF amplitude can be 6.4 kV, and the RF frequency can be about 1.2 MHz. It will be appreciated by those skilled in the art that such values for RF amplitude in accordance with the present teachings can be substantially greater than those by which quadrupole ion traps conventionally operate in a narrow bandpass, mass filter mode (e.g., as shown in FIG. 2).

Figure 4:
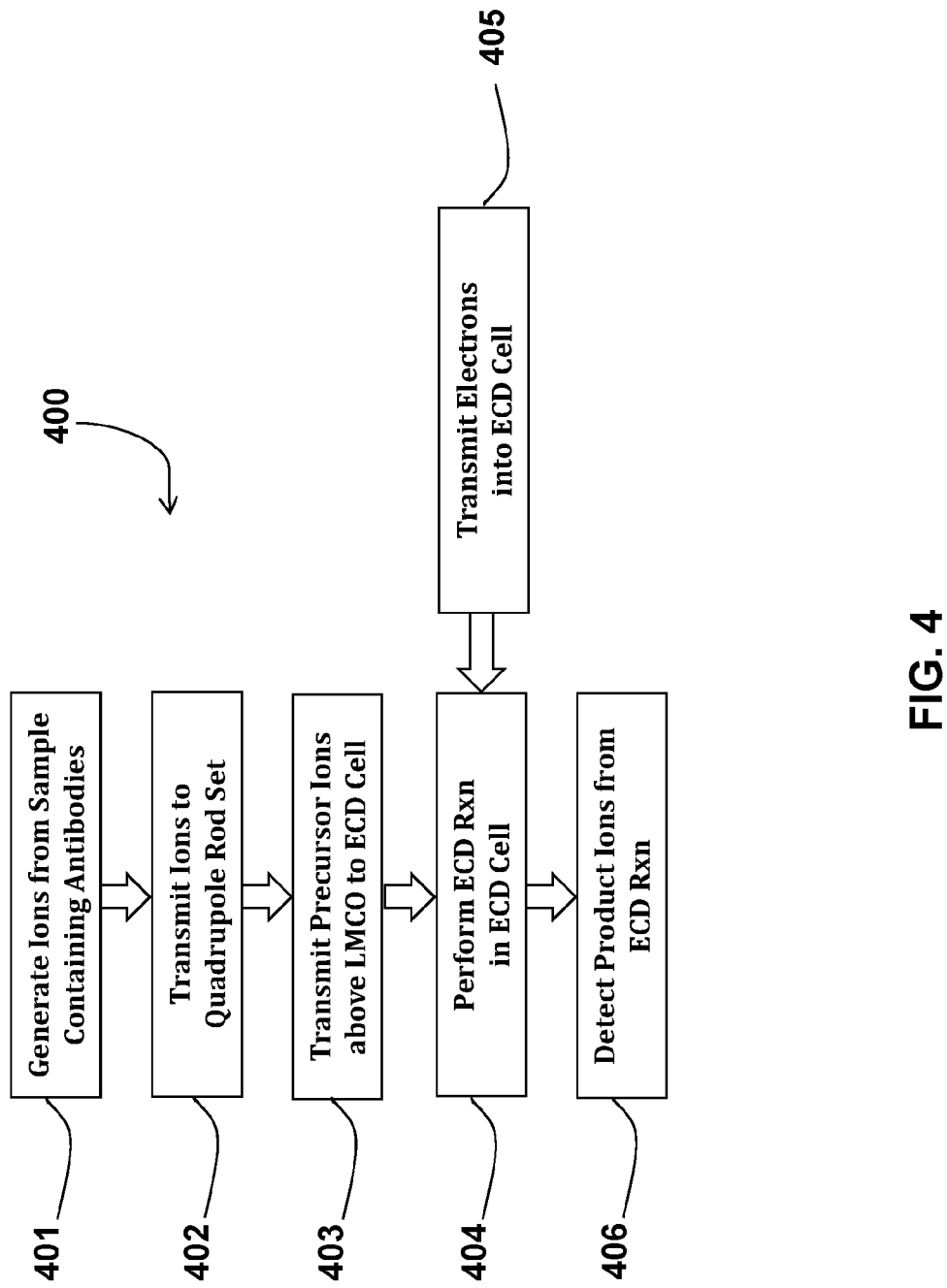
FIG. 4 depicts a flow chart of an exemplary method for performing ECD-based top down analysis of an antibody according to various aspects of the present teachings.

With reference now to FIG. 4, an exemplary method 400 for operating the mass spectrometer system of FIG. 1 in accordance with various aspects of the present teachings is depicted. As shown in step 401, the method 400 can begin by delivering a sample containing antibodies to the ion source 104, whereby the molecules within the sample are ionized. Once the molecules within the sample (including the antibodies) are ionized, these ions are transmitted to the quadrupole rod set 104, for example, through one or more ion lenses, mass analyzers, and/or differentially pumped vacuum stages (e.g., $Q_0$ or $Q_{jet}$) as shown in step 402. As the ions are transmitted into and through the quadrupole rod set 104, the various rods 104a-d have an RF signal applied thereto as shown in FIG. 3 such that the combination of the RF amplitude (V) and frequency (Ω) destabilize and discharge ions below the LMCO associated with this RF signal, while allowing those ions (including the relatively high m/z antibody ions) above the LMCO to be transmitted into the ECD cell (step 403). In accordance with the present teachings, it will be appreciated that operating the quadrupole rod set 104 in this RF-only mode can allow for the transmission of ions of the antibodies of interest to the ECD cell 110 even if the antibody ions exhibit different charge states (e.g., the same species of antibody, with one molecule being singly-charged and the other being doubly-charged). In step 404, these precursor antibody ions transmitted to the ECD cell 110 are then subjected to an ECD reaction (e.g., via interactions with electrons trapped within or transmitted through the ECD cell 110 in step 405), thereby resulting in the formation of product ions. In step 406, the ECD product ions are then detected by the detector 110 so as to generate an ECD product ion spectra, which can be analyzed as known in the art to reconstruct the antibody structure in a "top down" analysis.

The applicant's teachings can be even more fully understood with reference to the following examples and data presented in FIGS. 5A-C, which are provided to demonstrate but not limit the present teachings. As described below, the methods and systems disclosed herein selectively prevent ions exhibiting a m/z below a low mass cutoff (LMCO) from being transmitted to the downstream ECD cell.

Example 1

A sample was prepared comprising a humanized monoclonal IgG antibody (NIST-mAb) obtained from NIST. The sample was subjected to desalting and LC separation utilizing a desalting LC column (Waters) and then electrospray ionization and mass spectrometry using a research grade quadrupole-TOF system (SCIEX), modified to include an ECD cell as described in the article entitled "Electron Capture Dissociation in a Branched Radio-Frequency Ion Trap" published in Anal. Chem. 87(1): 785-792, which is incorporated by reference in its entirety. The ECD cell was installed between Q1 and Q2 of the mass spectrometer system. Typical electron beam irradiation time was 10 ms, and the electron beam intensity was tuned to obtain appropriate dissociation efficiency. The mass resolution of the TOF-MS was 35,000-47,000, which resolved isotope patterns of fragments up to Z 30+. FIG. 5A depicts the spectrum generated from the ionized sample, with the RF amplitude being selected to allow substantially all ions to be transmitted therethrough at 400 $V_{p-p}$. The spectrum of FIG. 5A includes a significant signal for ions exhibiting a m/z less than 500 as well as several significant peaks at about m/z 1520. With reference now to FIG. 5B, the amplitude of the RF signal applied to the quadrupole rod set was increased to 5 $kV_{p-p}$ (resolving DC voltage was set to 0 V) and the ions transmitted by Q1 were again detected (no ECD reactions were performed). As will be observed by comparing FIGS. 5A and 5B, by increasing the amplitude of the RF signal, Q1 prevented transmission of those ions exhibiting m/z less than about 1700. FIG. 7 depicts the ions detected upon performing ECD on the precursor ions transmitted from Q1 under the conditions of FIG. 5B. The low intensity peaks exhibiting a m/z less than about 2000 represent product ion fragments following ECD. Comparing FIGS. 5A and 5C, it will be appreciated that many of those product ion peaks observed in FIG. 5C would be obfuscated if the low m/z ions had not been removed in accordance with the present teachings, thereby making top down analysis of the antibody more challenging.

Those skilled in the art will know or be able to ascertain using no more than routine experimentation, many equivalents to the embodiments and practices described herein. By way of example, the dimensions of the various components and explicit values for particular electrical signals (e.g., amplitude, frequencies, etc.) applied to the various components are merely exemplary and are not intended to limit the scope of the present teachings. Accordingly, it will be understood that the invention is not to be limited to the embodiments disclosed herein, but is to be understood from the following claims, which are to be interpreted as broadly as allowed under the law.

The section headings used herein are for organizational purposes only and are not to be construed as limiting. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The invention claimed is:

1. A method for performing top down analysis of an antibody, comprising:
   utilizing an ion source to generate a plurality of ions from a sample containing at least one intact antibody,
   transmitting said plurality of ions through at least one quadrupole rod set while applying an adjustable RF signal thereto and without applying a resolving DC voltage to the quadrupole rod set so as to preferentially transmit precursor ions having an m/z value greater than a low mass cutoff of about 1500 m/z from the quadrupole rod set to an ECD cell;
   performing an ECD reaction in the ECD cell on said precursor ions;
   detecting reaction products from the ECD reaction.

2. The method of claim 1, wherein the at least one quadrupole rod set comprises a mass filter.

3. The method of claim 1, further comprising adjusting at least one of the amplitude and frequency of the adjustable RF signal such that the low mass cutoff is about 1700 m/z.

4. The method of claim 1, further comprising adjusting at least one of the amplitude and frequency of the adjustable RF signal such that the low mass cutoff is about 2000 m/z.

5. The method of claim 1, wherein the low mass cutoff is about 1700 m/z.

6. The method of claim 1, wherein the low mass cutoff is about 2000 m/z.

7. The method of claim 1, wherein at least a portion of said reaction products have an m/z below said low mass cutoff.

8. The method of claim 1, wherein performing an ECD reaction comprises introducing electrons into the ECD cell while transmitting said precursor ions therethrough.

9. The method of claim 1, wherein the precursor ions comprise ions of said antibody at a plurality of charge states.

10. The method of claim 9, wherein the ions of said antibody at a plurality of charge states exhibit at least two m/z in a range from about 2000 to about 4000.

11. A mass spectrometer system, comprising:
    an ion source for generating a plurality of ions from a sample containing intact antibodies;
    at least one quadrupole rod set extending along a central longitudinal axis and configured to receive said plurality of ions from said ion source through an inlet end and to transmit at least a portion of said ions through an outlet end, the quadrupole rod set comprising a first pair of elongate rods and a second pair of elongate rods disposed around and parallel to the central longitudinal axis;
    an ECD cell for receiving ions transmitted from the quadrupole rod set and within which said ions received from the quadrupole rod set are reacted with electrons to generate product ions therefrom;
    a detector for detecting said product ions; and
    a power system electrically coupled to the quadrupole rod set, said power system configured to provide an adjustable RF signal to the quadrupole rod set in the absence of without applying a resolving DC voltage to the quadrupole rod set so as to substantially prevent ions having a m/z value less than a low mass cutoff of about 1500 m/z from being transmitted from the quadrupole rod set to the ECD cell.

12. The system of claim 11, wherein the at least one quadrupole rod set comprises a mass filter.

13. The system of claim 11, wherein the quadrupole rod set is housed within a chamber maintained at a pressure less than about $1 \times 10^{-4}$ Torr.

14. The system of claim 11, wherein the power system is configured to provide the adjustable RF signal to the quadrupole rod set without applying the resolving DC voltage to the quadrupole rod set to substantially prevent ions having a m/z value less than a low mass cutoff of about 1700 m/z from being transmitted from the quadrupole rod set to the ECD cell.

15. The system of claim 11, wherein the power system is configured to provide the adjustable RF signal to the quadrupole rod set without applying the resolving DC voltage to the quadrupole rod set to substantially prevent ions having a m/z value less than a low mass cutoff of about 2000 m/z from being transmitted from the quadrupole rod set to the ECD cell.

16. The system of claim 11, further comprising a controller configured to increase the amplitude of the adjustable RF signal to increase the low mass cutoff.

17. The system of claim 11, wherein at least a portion of said product ions have an m/z below said low mass cutoff.

18. The system of claim 11, wherein said intact antibodies have an m/z in a range from about 2000 to about 4000.

19. The system of claim 11, further comprising an electron source for introducing electrons into the ECD cell.

20. The system of claim 11, wherein the amplitude of the adjustable RF signal is in a range from about 0.1 $kV_{p-p}$ to about 10 $kV_{p-p}$.

* * * * *